United States Patent [19]

Miller

[11] Patent Number: 4,532,816

[45] Date of Patent: Aug. 6, 1985

[54] SAMPLE VESSEL

[75] Inventor: Mark C. Miller, Chanhassen, Minn.

[73] Assignee: The Perkin-Elmer Corporation, Norwalk, Conn.

[21] Appl. No.: 516,827

[22] Filed: Jul. 25, 1983

[51] Int. Cl.³ .................. G01N 37/00; G01N 1/00
[52] U.S. Cl. .................. 73/864.91; 73/864.84; 250/288; 414/217
[58] Field of Search ............... 250/288; 414/217; 73/864.81, 864.82, 864.83, 864.84, 864.85, 864.86, 864.87, 864.91

[56] References Cited

U.S. PATENT DOCUMENTS

| | | | |
|---|---|---|---|
| 3,117,223 | 1/1964 | Brunnee | 250/288 X |
| 3,590,243 | 6/1971 | Perrin et al. | 250/288 |
| 3,596,087 | 7/1971 | Heath | 250/288 X |
| 3,842,266 | 10/1974 | Thomas | 250/288 |
| 4,049,134 | 9/1977 | Dolgen | 73/864.82 |
| 4,067,697 | 1/1978 | Polaschegg | 73/864.81 |
| 4,308,756 | 11/1982 | Robinson et al. | 73/864.82 X |
| 4,411,575 | 10/1983 | Miller | 73/864.81 X |
| 4,412,771 | 11/1983 | Gerloch et al. | 414/217 |

FOREIGN PATENT DOCUMENTS

| | | | |
|---|---|---|---|
| 2548891 | 5/1977 | Fed. Rep. of Germany | 250/288 |
| 2469251 | 5/1981 | France | 414/217 |
| 27693 | 3/1977 | Japan | 250/288 |

Primary Examiner—Stewart J. Levy
Assistant Examiner—Tom Noland
Attorney, Agent, or Firm—E. T. Grimes; J. D. Crane

[57] ABSTRACT

A sample vessel for carrying a sample and storing same in a high vacuum. The vessel includes a hollow body which is open at one end. A specimen carrier plate is coupled by a translating mechanism so that it can slide in and out of said hollow body through the opening. An O-ring seal is provided to seal the carrier plate to the vessel thereby sealing the specimen carried thereby inside the hollow body which can then be evacuated leaving a high vacuum inside.

22 Claims, 3 Drawing Figures

SAMPLE VESSEL

BACKGROUND OF THE INVENTION

The present invention generally relates to a sample vessel and, in particular, relates to such a vessel which includes means for simultaneously controlling both the sealing thereof and the delivery of a sample therefrom. In a preferred embodiment the vessel is adapted for use in conjunction with an ultra-high vacuum analytical instrument.

As the techniques for analytically determining the elemental and/or chemical nature of sample surfaces develop, the purity requirement of samples, or specimens, to be tested also increases. One such analytical technique is generally known as ESCA (Electron Spectroscopy for Chemical Analysis). In an ESCA instrument, the surface of a sample is bombarded with soft X-rays which liberate photoelectrons from the sample surface. All elements, with the exception of hydrogen, which are present in detectable amounts within the X-ray absorption volume generate well defined peaks in the photoelectron energy distribution. The elemental or chemical composition of the surface is then determined from the peaks in the energy distribution. The ESCA technique provides quite accurate surface information and, because of its sensitivity, it is imperative that the surface undergoing analysis be as free as possible from any contaminants or contamination. As used herein the word "surface" refers to the first few atomic layers of the sample undergoing analysis.

Generally, in order to have an ESCA examination of a specimen the specimen is isolated, or prepared, and mounted on a specimen holder remote from the instrument. The prepared specimen is then placed in a sample vessel for transport to a laboratory whereat it is inserted into an ESCA instrument and the analysis is performed.

Almost any sample to be analyzed is susceptible to some form of contamination right from the moment it is isolated from its source and continues to be susceptible until it is placed in the ultra-high vacuum environment of the analytical instrument. Ideally, of course, a sample is isolated in close physical proximity with the instrument. However, such convenient physical proximity is rarely available in the practical world. This condition exists for a number of obvious reasons, not the least of which is the considerable expense of the analytical instrument itself in addition to the relatively small number of trained instrument operators. Consequently, samples which are to be analyzed are usually required to be transported over substantial distances and times after they are isolated. One conventional precaution used when isolating highly contaminative specimens, is the use of a "glove box". By use of such a device the sample is isolated and packaged in an inert atmosphere. When the sample is removed from the shipping package and inserted into the instrument, the entire entry chamber must be evacuated to an ultra-high vacuum level prior to exposing the packaged sample thereto. Such a procedure is not only time consuming, since the creation of an ultra-high vacuum within an analytical instrument takes a considerable amount of time, but also exposes the sample to be tested to a potentially contaminating atmosphere until the ultra-high vacuum is achieved. Further, once the entry chamber reaches an ultra-high vacuum level and the vessel is opened, the ultra-high vacuum is lost due to the atmosphere within the vessel and, hence, must be reestablished.

Nevertheless, such precautionary procedures are unacceptable when the sample is a chemically active element, i.e., one which can be easily contaminated by the least exposure to any environment or an element which can be hazardous, i.e., explosive, when exposed to such an ambient. Sample vessels for transporting such specimens are known in the art wherein the vessel itself can be inserted into the ultra-high vacuum system and maintained in that position prior to exposing the sample thereto.

One such vessel is described in U.S. Pat. Ser. No. 259,723, filed May 1, 1981, now U.S. Pat. No. 4,411,575 and assigned to the assignee hereof. As described therein, a vessel includes a sample mounting block upon which a sample holder can be secured. The device includes a lid into which the mounting block can be placed and hermetically sealed.

In use, one end of the vessel is inserted into an instrument entry chamber wherein the mounting block is removed, together with the specimen carried thereon, which specimen is then removed by a forked sample receiving mechanism. Although such a device performs quite well for the purpose intended, it inherently is somewhat disadvantageous in that the atmosphere within the vessel itself is merely inert and is not capable of being provided with an ultra-high vacuum. This is disadvantageous primarily because of the length of time necessary to reduce even an entry chamber to an ultra-high vacuum level after the vessel is opened. That is, pumping must usually be continued to remove the inert gases within the vessel.

Other vessels are available which remotely control the opening of the vessel once inside the ultra-high vaccum chamber by a mechanism integral with the vessel itself. Such vessels require multiple controls i.e., a first control for the opening and closing thereof and a second control, also integrated within the vessel, for transporting the sample into, or out of, the vessel proper. Such a sample transfer vessel is cumbersome to operate and subject to failures due to the multiplicity of control related moving parts therein.

From the above, it is quite clear that there is a considerable need for an easily operated sample vessel within which a sample can be transported under an ultra-high vacuum.

SUMMARY OF THE INVENTION

Accordingly, one object of the present invention is to provide a sample vessel which is easily operated and which can be evacuated to an ultra-high vacuum.

This object is accomplished, at least in part, by a sample vessel having means for simultaneously controlling both the sealing and unsealing of the vessel itself and the delivery from and receiving of a sample therewithin.

Other objects and advantages will become apparent to those skilled in the art from the following detailed specification read in conjunction with the appended claims and the drawing attached hereto.

BRIEF DESCRIPTION OF THE DRAWING

The drawing, not drawn to scale, includes.

DETAILED DESCRIPTION OF THE INVENTION

Figure 1:
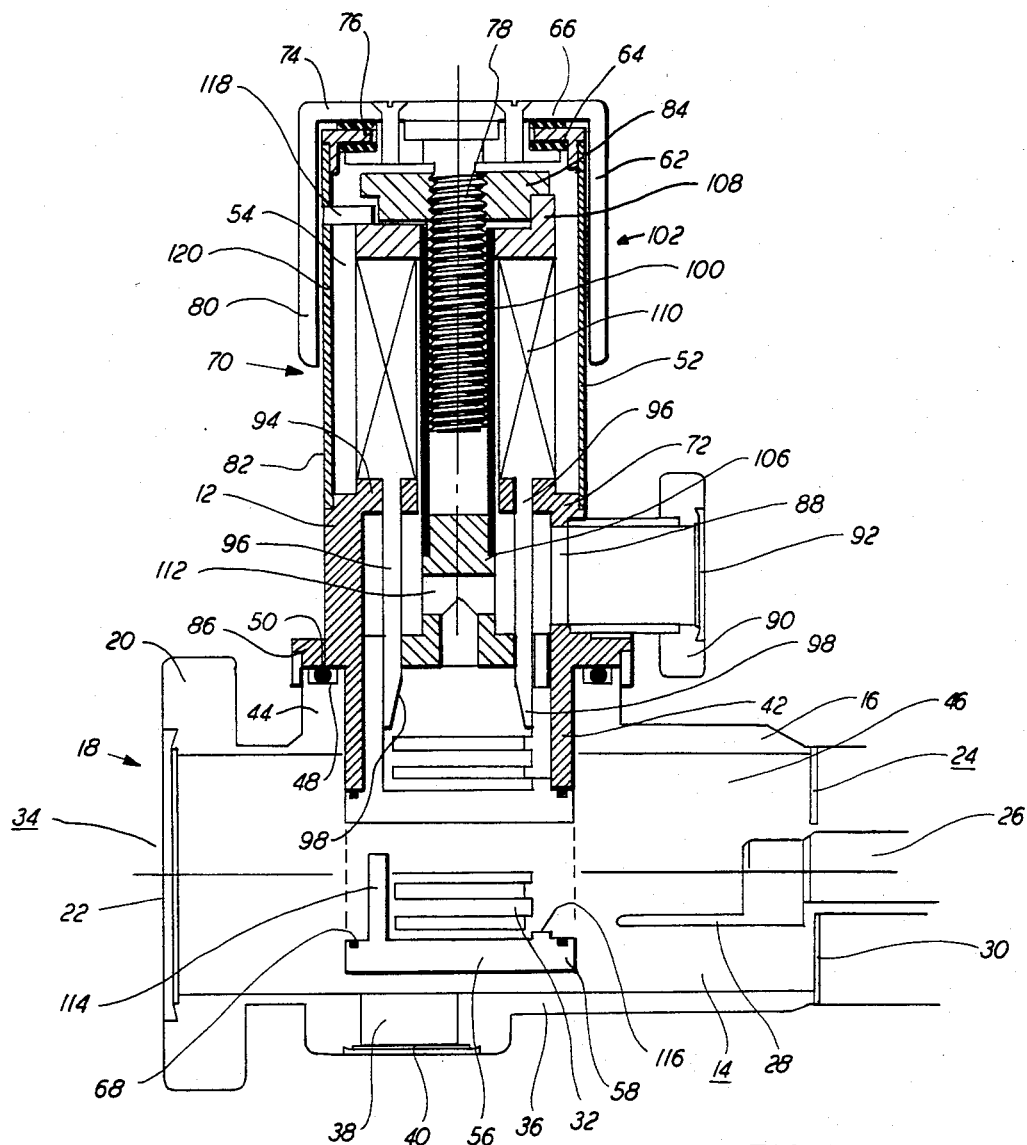
FIG. 1, which is a partial cross-sectional view of a vessel embodying the principles of the present invention in conjunction with an introduction system of an ultra-high vacuum analytical instrument.

An assembly, generally indicated at 10 in FIG. 1, includes a sample vessel 12, embodying the principles of the present invention and an introduction system 14 for an ultra-high vacuum analytical instrument. As shown, the introduction system 14 includes a hollow, preferably cylindrically shaped, member 16 having, at one end 18 thereof, a flange 20 for connection to an ultra-high vacuum analytical instrument. An isolation gate valve 22 is provided at the one end 18 for regulating communication between the introduction system 14 and the analytical instrument. At the other end 24 of the hollow member 16, a pickup fork mechanism 26 is provided which includes a two-pronged fork 28 extendable through a vacuum sealed opening 30, such as a bellows. In operations, the sample pickup fork 28 is extended into the hollow member 16 to retrieve a specimen holder 32, for example, from the sample vessel 12 and subsequently deliver it to an analysis chamber 34 of the instrument.

The holler member 16 further includes, through one wall 36 thereof, a system pumping port 38 having an isolation valve 40 associated therewith, via which the introduction system 14, per se, is reduced to an ultra-high vacuum. In addition to the system pumping port 38, the introduction system 14 includes a samples vessel receiving opening 42 through the wall 36 thereof. The sample vessel receiving opening 42, in this embodiment, includes a rim-like extenstion 44 thereabout upon which the sample vessel 12 is placed. As more fully explained hereinafter, the height of the extension 44 is cooperatively adapted with a ridge extending about the outside of the vessel 12. Hence, when the ridge is positioned on the rim extension 44, one end of the vessel extends into the cavity 46 of the hollow member 16 of the introduction system 14. Preferably, the rim extension 44 includes a peripheral groove 48 wherein a system seal 50, in the form an O-ring for example, is positioned. The O-ring seal 50 is designed so as to be compressed when a vacuum is drawn on the introduction system 14 thereby sealing the interface between the vessel 12 and the introduction system 14.

In the preferred embodiment, the sample vessel 12 includes a housing 52 having an opening 54 therethrough within which a carrier plate 56 is slideably positioned. The plate 56 includes a means 58 for securing and supporting a specimen holder 32. The sample vessel 12 further includes a means 62 for translating the carrier plate 56 longitudinally within the housing 52. The sample 12 vessel additionally includes, at one end 64 thereof, a means 66 for simultaneously controlling both the means 62 for longitudinal translation and a means 68 for sealing whereby, when a specimen holder 32 is placed on the carrier plate 56 and transported into the vessel 12, the housing 52 is simultaneously sealed. In the preferred embodiment, the sealing means 68 includes a peripheral groove 65 formed in the carrier plate 56 proximate the vessel 12. The groove 65 is provided with an O-ring 67, or the like, and aligned with the bottom edge 69 of the housing 52. Consequently, when the plate 56 is withdrawn into the housing 52 the O-ring 67 is compressed and seals the one end 64 of the vessel 12.

Figure 2:
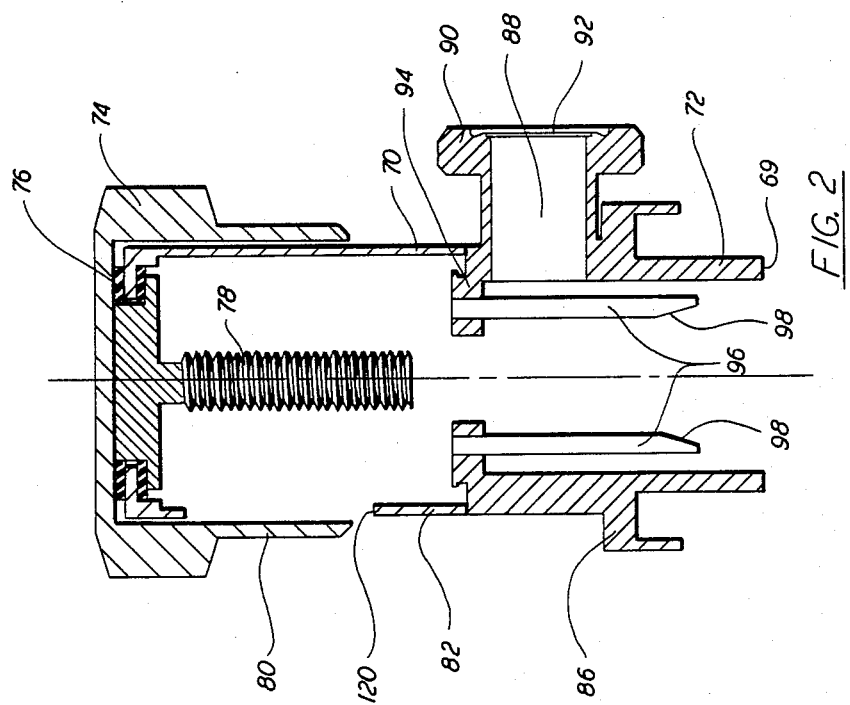
FIG. 2, is a partial cross-sectional view of a typical housing for the vessel shown in FIG. 1.

In the preferred embodiment, the housing 52, as more clearly shown in FIG. 2, includes an upper segment 70 and a lower segment 72, which upper segment 70 includes the simultaneously controlling means 66 in the form of a knob 74 rotatably mounted on thrust bearing 76, which knob 74 is affixed to a drive screw 78 axially extending into the opening 54 of the upper segment of the housing 52. For reasons more fully explained below, the knob 74 preferably includes an overhanging portion 80 which extends about the outer wall 82 of the housing 52 by a preselected length. A drive nut 84 is threaded onto the drive screw 78 and translates longitudinally within the housing 52 in response to the rotation of the knob 74.

Preferably, the lower segment 72 of the housing 52 includes an externally protruding peripheral ridge 86 adapted to seat upon the extending rim 44 of the introduction system 14. The lower segment 72 of the housing 52 includes a selectively accessable vacuum port 88 having a flange 90 distal therefrom and which preferably, although not necessarily, includes an isolation valve 92 associated therewith. By this port 88, the interior of the lower segment 72 of the housing 52 can be placed at an ultra-high vacuum and maintained thereat until the seal is broken. The lower segment 72 of the housing 52 also includes an inwardly protruding shelf 94 and carries therewith at least two clamping pins 96 which clamping pins 96 include a beveled end 98 proximate the carrier plate 56.

Figure 3:
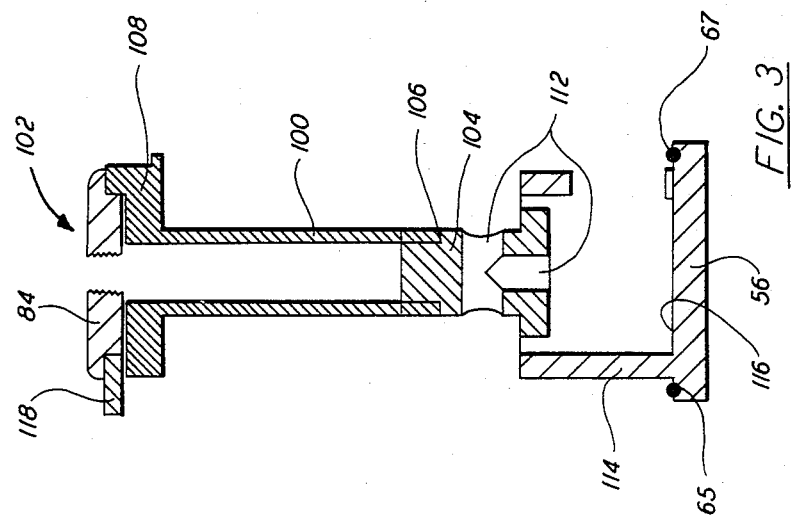
FIG. 3 is a partial cross-sectional view of a mechanism for use in the vessel shown in FIG. 1.

As shown in FIG. 3, the vessel 12 further includes a central longitudinaly extending tube 100 surrounding, at one end 102, the drive screw 78. A carrier plate assembly 104, including the carrier plate 56, is inserted into the other end 106 of the tube 100 and forms a vacuum tight seal thereat. Preferably, the tube 100 further includes a plate 108 which interfaces with the drive nut 84 and is longitudinally positionally controlled thereby. In the preferred embodiment, the tube 100 is surrounded by a collapsible bellows 110 extending between the interface plate 108 and the upper surface of the shelf 94 of the lower segment 72 of the housing 52. Thus, the bellows 110 effectively seals the joints between the upper and lower segments, 70 and 72 respectively, thereby preventing the loss of any vacuum formed within the lower segment 72.

The carrier plate assembly 104 includes openings 112 therein whereby the pumping port 88 is in cummunication with the interior of the lower segment 72 of the housing 52 within which the specimen holder 32 is positioned. The carrier plate 56 is integrally and rigidly affixed to the carrier plate assembly 104 via an arm member 114 extending between the carrier plate 56 and the assembly 104. The carrier plate 56 includes a recess 116 which is cooperatively dimensioned to accept a specimen holder 32 therein such that movement of the holder 32 in the plane of the carrier plate 56 is minimized.

In operation, by rotating the knob 74, the carrier plate 56, having a specimen holder 32 thereon, is extended downwardly from the vessel 12 into the cavity 46 of the introduction system 14 wherein the specimen holder 32 is removed by the sample pickup fork 28 for subsequent introduction, via the isolation gate valve 22, into the analytical instrument. As an aid in positioning of the carrier plate 56, i.e., alignment with the prongs of the pickup fork 28, a position indicator 118 is provided between the drive nut 84 and the interface plate 108. The position indicator 118 is carried longitudinally therewith such that it can be readily observed through a slot 120 in the wall 82 of the upper segment 70 of the housing 52.

By known machining techniques, the drive screw 78 and the various lengths of the moving elements are coordinated so that when the position indicator 118 is just observable at the bottom of the overhanging portion 80 of the knob 74 at the wall 82 of the housing 52, the carrier plate 56 is extended into the cavity 46 of the introduction system 14 to a level whereat the specimen holder 32 is aligned with the prongs of the pickup fork 28.

The sample pickup fork 28 can then be extended to support the specimen holder 32 and the knob 74 further rotated, for example until the entire thickness of the position indicator 118 becomes observable. In the preferred embodiment, this is indicative that the carrier plate 56 is lowered beyond the depth of the recess 116 therein and hence, the specimen holder 32 is now supported only by the sample pickup fork 28. Thus, the specimen holder 32 is free from the carrier plate 56. The sample pickup fork 28 is withdrawn, carrying the specimen holder 32 therewith and the knob 74 counterrotated to withdraw the carrier plate 56 and re-seal the vessel 12. Whereupon the sample pickup fork 28 can be extended through the introduction system 14 into the instrument and the analysis of the specimen proceeds.

The sample vessel 12 can be fabricated using well known machining techniques. Preferably, the vessel 12 is formed from stainless steel and the upper and lower segments, 70 and 72 respectively, are welded together. In one embodiment, the machined moving parts are formed so that the carrier plate 56 has a travel length of about 2.5 cm whereby it can be extended slightly more than midway into the cavity 46 of a 3.8 cm inside diameter hollow member 16. Futher, the depth of the recess 116 in the carrier plate 56 is designed to be less than the height of the position indicator 118. Thus, when the position indicator 118 is fully observed the specimen holder 60 is supported solely by the pickup fork 28 and is clear of the recess 116.

One distinct advantage of this sample vessel 12 is that a specimen can be loaded therein in a glove box and the knob 74 rotated so as to withdraw the carrier plate 56 against the lower segment 72 of the housing 52 to form a vacuum seal. Further, the clamping pins 96 are arranged so as to subtantially prevent longitudinal movement of the specimen holder 32 so long as the carrier plate 56 is withdrawn. The lower segment 72 can then be pumped, via the pumping port 88, to create an ultrahigh vacumm within the housing 52 and sealed, via the valve 92, to maintain that vacuum. Thus, a sample within the vessel 12 is not only sealed from the contaminating effects of the outside environment but is also under an ultra-high vacuum environment whereby contamination by the sealed ambient is at a minimum. Another advantage of such a vessel 12 is that, by measn of the clamping pins 96, the specimen holder 32 is secured in place and the vessel 12 can be shipped long distance or stored for long periods of time without disturbing the sample specimen holder 32. Consequently, so long as the specimen is rigidly affixed to the specimen holder 32, there is little danger of sample loss, fracture or other damage.

Still another advantage of the vessel 12 is that its use allows a specimen to be from one analysis system to another without removing that specimen from an ultra-high vacuum. Specifically, the above-described delivery procedure is reversed to re-insert the specimen holder 32 into the vessel 12 whereupon it is sealed in an ultra-high vacuum. The vessel 12 can then be removed from the introduction system 14 and re-inserted therein later or inserted in another analytical instrument.

Although the above sample vessel and assembly have been described with respect to a specific embodiment, other arrangments and configurations will become apparent to those skilled in the art to which this application pertains. Consequently, this description is considered exemplary and not limiting and that the present invention is limited only by the appended claims and the reasonable interpretation thereof.

What is claimed is:

1. A sample vessel comprising:
    an elongated hollow housing having two ends, one end thereof having an opening therethrough;
    a carrier plate slidably positioned within said housing, said plate including means for supporting a specimen holder;
    means for sealing said housing opening;
    means, within said housing, for longitudinally translating said carrier plate; and
    means distal said opening and located relatively closer to the end of said housing opposite to the open end to simultaneously control said translating means and said sealing means to seal said housing when a specimen holder carried by said carrier plate is within said housing, the seal being such that when said housing gets sealed the specimen holder is located interior to the sealed exterior of said housing.

2. Sample vessel as claimed in claim 1 further comprising:
    means for selectively accessing the interior of said housing whereby a vacuum can be created and maintained therein.

3. Sample vessel as claimed in claim 2 wherein said selective accessing means includes:
    a port extending from the wall of said housing, said port providing gaseous communication between said housing and the external ambient; and
    an isolation valve across said port to control said gaseous communication.

4. Sample vessel as claimed in claim 3; further comprising;
    means, integral with said port for connecting a vacuum pumping system to said port whereby said housing can be evacuated.

5. Sample vessel as claimed in claim 1 further comprising:
    means for sealing said other end of said housing.

6. Sample vessel as claimed in claim 5 wherein said housing includes:
    an inwardly projecting shelf, said shelf defining an upper segment and a lower segment within said housing; and said other end sealing means includes;
    a collapsible bellows extending into said upper segment from said shelf.

7. Sample vessel as claimed in claim 1 further comprising:
    means for indicating the position of said carrier plate.

8. Sample vessel as claimed in claim 7 wherein said position indicating means includes:

a rigid member, said member being synchronously translated with said carrier plate and viewable through a slot in a wall of said housing.

9. Sample vessel as claimed in claim 1 further comprising:
means, within said housing and extending toward said carrier plate, for clamping said specimen holder in a fixed position within said housing when said specimen holder is on said carrier plate.

10. Sample vessel as claimed in claim 9 wherein said housing includes:
an upper segment and a lower segment, said lower segment having an inwardly projecting shelf at the end thereof proximate said upper segment; and
a plurality of clamping pins extending from shelf into said lower segment, said pins defining said specimen holder clamping means.

11. Sample vessel as claimed in claim 10 wherein each one of said plurality of clamping pins includes a beveled surface at the end thereof extending into said lower segment, said pins extending a distance so as to firmly contact said sample holder when said vessel is sealed.

12. Sample vessel as claimed in claim 1 wherein said hollow housing includes an upper segment and a lower segment.

13. Sample vessel as claimed in claim 12 wherein said upper segment includes:
a knob, said knob being rotatably affixed to the end of said upper segment distal said lower segment;
a drive screw, said drive screw being affixed to said knob and extending into said upper segment therefrom.

14. Sample vessel as claimed in claim 13 wherein said longitudinal translating means includes:
a drive nut threaded onto said drive screw, said drive nut being longitudinally translated therealong in response to rotation of said knob; and
means, interconnecting said drive nut and said carrier plate, for transferring said longitudinal translation of said drive nut to said carrier plate.

15. Sample vessel as claimed in claim 14 wherein said translation transfer means includes:
a tube, said tube extending from said drive nut in said upper segment into said lower segment; and
a carrier plate assembly, including said carrier plate, affixed to said tube in said lower segment.

16. Sample vessel as claimed in clain 15 further comprising:
means for gaseoulsy isolating said upper and lower segments from each other.

17. Sample vessel as claimed in claim 16 wherein said gaseous isolating means includes:
a collapsible bellows substantially completely surrounding said tube and extending between said drive nut and an inwardly protruding shelf at the end of said lower segment proximate said upper segment.

18. Sample vessel as claimed in clain 12 further comprising:
means for gaseously isolating said upper and lower segments from each other.

19. Sample vessel as claimed in claim 1 wherein said means for sealing one end of said housing includes:
a peripheral groove about said carrier plate, said grovve being aligned with an edge of said housing; and
a compressible ring, said ring being positioned within said groove in said carrier plate.

20. An assembly for introducing a sample; said assembly comprising:
an introduction system; said system including a hollow member having an opening in one wall thereof;
a rim extending about said opening away from wall;
means for evacuating said member;
a sample vessel having a housing, said housing having a peripheral ridge extending from an external wall thereof; and
means for sealing the interface between said ridge and said rim when said member is evacuated.

21. Assembly as claimed in claim 20 further comprising:
means, associated with said sample vessel, for delivering a specimen holder into said opening; and
means, associated with said introduction system, for removing said specimen holder from said sample vessel.

22. Assembly as claimed in claim 21 wherein said specimen holder removing means includes;
a pronged pickup fork, said fork being extendable into said opening from one end of said system.

* * * * *